United States Patent [19]

Tomita et al.

[11] Patent Number: 5,310,473
[45] Date of Patent: May 10, 1994

[54] REMOVABLE SAMPLE TESTING MEMBER FOR USE IN MEASURING ION CONCENTRATION

[75] Inventors: Katsuhiko Tomita, Ohtsu; Akemi Mototsune, Matsue; Junji Kojima, Nara, all of Japan

[73] Assignee: Horiba Ltd., Kyoto, Japan

[21] Appl. No.: 102,092

[22] Filed: Aug. 4, 1993

Related U.S. Application Data

[63] Continuation of Ser. No. 456,845, Dec. 27, 1989, Pat. No. 5,248,403, which is a continuation of Ser. No. 99,294, Sep. 17, 1987, abandoned.

[30] Foreign Application Priority Data

Mar. 19, 1986 [JP] Japan ................ 61-63564
Mar. 19, 1986 [JP] Japan ................ 61-63565
Dec. 11, 1986 [JP] Japan ................ 61-191495

[51] Int. Cl.$^5$ ............................................ G01N 27/26
[52] U.S. Cl. ................................... 204/414; 204/420; 204/416; 204/433; 204/435
[58] Field of Search ............ 204/414, 420, 416, 433, 204/435

[56] References Cited

U.S. PATENT DOCUMENTS

| | | | |
|---|---|---|---|
| 3,410,778 | 2/1965 | Krasberg | 204/195 |
| 3,833,495 | 9/1974 | Grubb | 204/195 R |
| 3,911,901 | 10/1975 | Niedrach | 128/2 E |
| 3,957,612 | 5/1976 | Niedrach | 204/195 R |
| 4,053,381 | 10/1977 | Hamblen | 204/195 R |
| 4,105,509 | 9/1978 | Jungck | 204/195 R |
| 4,133,735 | 1/1979 | Afromowitz | 204/433 |
| 4,225,410 | 9/1980 | Pace | 204/403 |
| 4,227,974 | 10/1980 | Petersen | 204/416 |
| 4,269,685 | 5/1981 | Parker | 204/195 P |
| 4,280,889 | 7/1981 | Szonntagh | 204/195 R |
| 4,282,079 | 8/1981 | Chang | 204/195 G |
| 4,318,884 | 3/1982 | Suzuki | 422/63 |
| 4,340,457 | 7/1982 | Kater | 204/195 R |
| 4,454,007 | 6/1984 | Pace | 204/416 |
| 4,468,271 | 8/1984 | Pierson | 204/416 |
| 4,549,951 | 10/1985 | Knudson | 204/416 |
| 4,592,824 | 6/1986 | Smith | 204/416 |
| 4,713,165 | 12/1987 | Conover | 204/403 |
| 4,797,188 | 1/1989 | Tomita | 204/414 |
| 4,816,132 | 3/1989 | Kotani | 204/414 |
| 4,872,966 | 10/1989 | Kotani | 204/414 |
| 4,980,043 | 12/1990 | Tomita | 204/414 |

FOREIGN PATENT DOCUMENTS 2541462 2/1983 France.

*Primary Examiner*—John Niebling
*Assistant Examiner*—Bruce F. Bell
*Attorney, Agent, or Firm*—Price, Gess, & Ubell

[57] ABSTRACT

An improved compact ion-concentration measuring apparatus having a removable sample testing module with gelatinized electrodes. The gelatinized portion of the electrodes can be formed with a jelly containing an acrylic polymer with sodium.

8 Claims, 7 Drawing Sheets

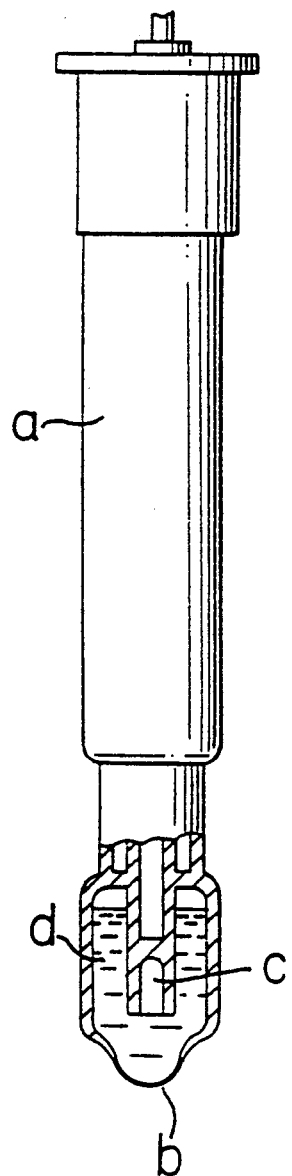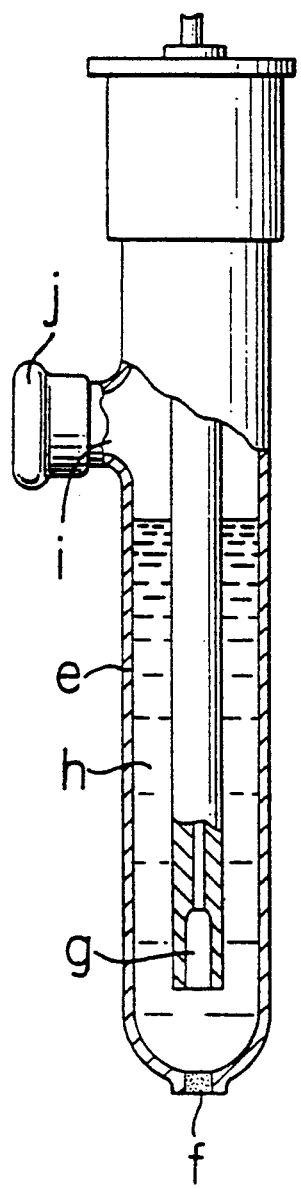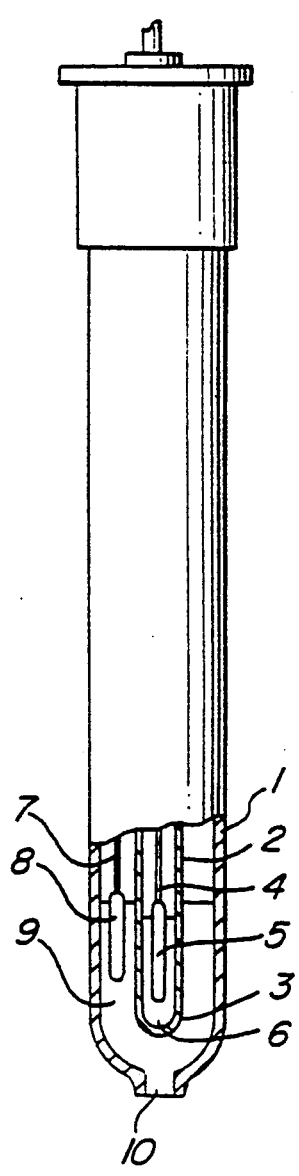

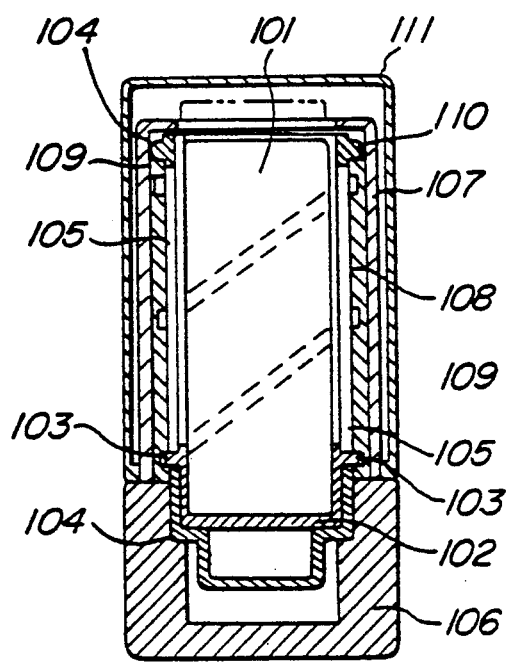
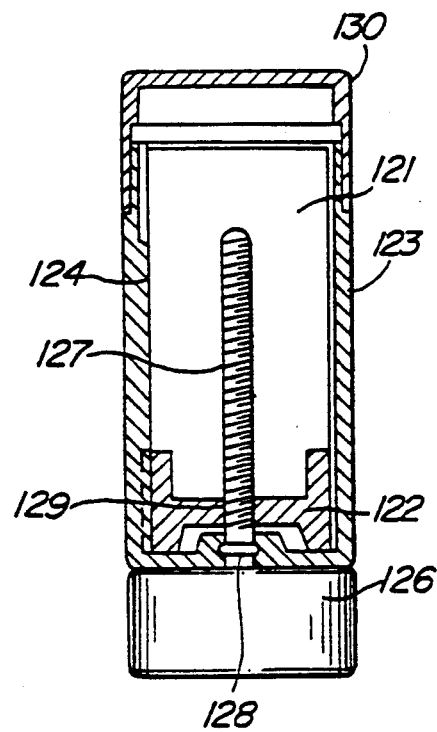
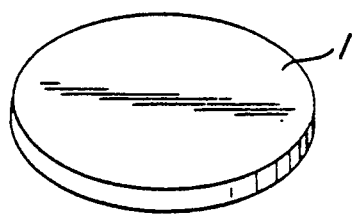
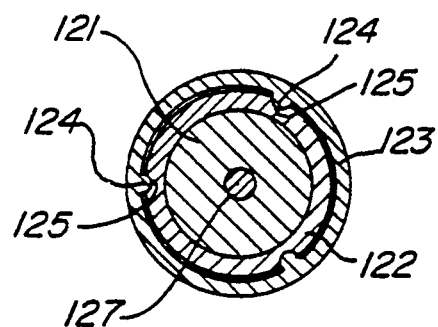

REMOVABLE SAMPLE TESTING MEMBER FOR USE IN MEASURING ION CONCENTRATION

This is a continuation of prior application Ser. No. 07/456,845, filed on Dec. 27, 2989, now U.S. Pat. No. 5,248,403 for a GELATINIZED MEMBER FOR USE IN ELECTRODES MEASURING ION CONCENTRATION, which application is a continuation of prior application Ser. No. 07/099,294, filed on Sep. 17, 1987, now abandoned.

BACKGROUND OF THE INVENTION

1. Field of the Invention

The present invention relates to an ion-measuring electrode device including a gelatinized member which can be used as internal solution in the electrode structure, as an element in the preservation of an electrode or as a reference for the calibration of a glass electrode. The gelatinized member can be used for either the measuring ion electrode or the reference electrode and the like (hereinafter called generally an electrode for measuring ions) particularly in the case where the electrode for measuring ions is constructed as a small-sized planar sheet that can be mounted on removable sample testing modules.

2. Description of the Prior Art

A prior art glass electrode for measuring ion concentrations, such as pH, pNa and the like, is shown in FIG. 1 and comprises a supporting cylinder or pipe "a" formed of an electrically insulating glass, an ion-response glass membrane "b" which is response to pH, pNa and the like having a semispherical shape formed at a pointed end of said supporting pipe "a" for example, by the balloon method so as to be adhered to the pointed end, an internal electrode "c" comprising for example an Ag wire, having a surface coated with AgCl and positioned in the supporting pipe "a" and an internal solution "d" comprising, for example, a 3.3 M-aqueous solution of KCl supersaturated by AgCl with a phosphoric acid-buffer solution added and enclosed in said internal electrode "c". In addition, another prior reference electrode has a supporting cylinder or pipe "e" formed of an electrically insulating glass, a liquid junction member "f" formed of, for example, inorganic sintered porous substances, organic high molecular porous substances and the like impregnated with KCl positioned in a hole formed in a pointed end portion of the supporting pipe "e", an internal electrode "g" comprising an Ag wire having a surface coated with AgCl in the same manner as in the above described glass electrode, and also provided in the supporting pipe "e", and finally an internal solution "h" comprising, for example, a 3.3 M-aqueous solution of KCl supersaturated by AgCl with a phosphoric acid-buffer solution added and enclosed in the internal electrode "g" as shown in FIG. 2. In referring to FIG. 2, "i" designates an internal solution-replenishing port having a cap "j" which is provided in the supporting pipe "e" so as to replenish any internal solution "h" that has been consumed.

These prior glass electrodes and reference electrodes have exhibited problems in that they are relatively large-sized and are difficult to mass-produce, so that not only are they remarkably expensive in the manufacture thereof but also they are not convenient in a measuring operation. Additionally, it is frequently necessary to preserve the glass electrode in pure water and the reference electrode in a 3.3 M-aqueous solution of KCl, which is the same as the internal solution, even while they are not being used.

Furthermore, the calibration (for example, pH calibration) of a glass electrode is carried out by the use of a standard solution (in short, a phthalic acid-standard solution having a pH of 4, neutral phosphoric acid-standard solution having a pH of 7 and sodium borate-standard solution having a pH of 9), however, a relatively large amount of each standard solution is required and also a vessel (beaker and the like) for receiving the standard solution is required. In addition, if these standard solutions are left unattended in an opened condition, they are apt to change in concentration, deposit crystals and deteriorate, so that it is considerably difficult to preserve them in an excellent condition for a long time period. Accordingly, it is required to exchange the standard solutions at a relatively high frequency, so that they have been remarkably troublesome in use and also uneconomical.

A gelatinized salt solution for a reference electrode is disclosed in Japanese Patent Publication Open to Public Inspection No. Sho 47-7749. A compound electrode for use in the measurement of pH is disclosed in Japanese Patent Examined Publication No. Sho 47-45317. This electrode comprises an inside cylinder enclosing an internal electrode for use in the measurement and a gelatinized internal solution therein.

In a reference electrode as disclosed in Japanese Patent Publication Open to Public Inspection No. Sho 47-7749, an internal solution is gelatinized, so that the internal solution is not consumed from a liquid junction. However, merely a salt solution is gelatinized with a gelatinizer, so that a problem occurs in that a surface of the liquid junction becomes dried when the reference electrode is not used. Accordingly, it is necessary to cut off an end portion of the gelatinized internal solution together with a tube after each use of the reference electrode to renew the liquid junction. Japanese Patent Examined Publication No. Sho 47-45317 discloses an electrode having an internal solution comprising neutral phosphate and potassium chloride gelatinized with agar-agar or gelatine. However, since the internal solution disclosed in the above described, both Japanese Patents are prepared by merely gelatinizing the internal solution with a gelatinizer, problems occur in that when it is left unattended in air of normal temperature, it is dried, so that many problems occur in packing and preservation. Thus, the prior art is still seeking an improved compact ion concentration measuring apparatus.

SUMMARY OF THE INVENTION

The present invention relates to an improved ion-measuring device having a gelatinized member for use in an electrode for measuring the ions which can eliminate the above conventional defects. The invention includes gelatinizing an appointed solution, such as an internal solution, a buffer solution, an ion-adjusting solution or combinations thereof, with a gelatinizer and adding a gel-evaporation inhibitor to the gelatinized solution.

The present invention can be configured as a handheld meter such as a pH meter with a convenient digital output and a replaceable electrode assembly. The electrode assembly can be arranged in a planar configuration with both the reference electrode and the ion-measuring electrode positioned on the same plane.

According to the present invention, a remarkably compact thin sheet-type electrode for measuring ions that is not only superior in operation and in maintenance but can be easily replaced is provided. In addition, the possibility of easily and economically carrying out the preservation of a glass electrode portion and a reference electrode portion of a sheet-type electrode for measuring ions as well as the calibration of the glass electrode portion is provided by the present invention.

Finally, an improved calibration reference can cooperate with the ion-measuring meter of the present invention.

BRIEF DESCRIPTION OF THE DRAWINGS

FIG. 1 is a partial cut-away view of a prior art glass electrode;

FIG. 2 is a partial cut-away view of another prior art glass electrode;

FIG. 3 is a partial cut-away view of a compound electrode according to the present invention;

FIG. 12 depicts a sectional view of a calibrating standard sample having a rod-like gelatinized standard solution 101 which may be rotated into and out of the housing for use in a calibration operation;

FIGS. 13 and 14 show a second preferred embodiment of a calibrating standard sample according to the present invention;

FIG. 15 depicts a gelatinized member for use in an internal solution for use in sheet-type electrodes like that depicted in FIGS. 6-8;

DESCRIPTION OF THE PREFERRED EMBODIMENTS

Figure 4:
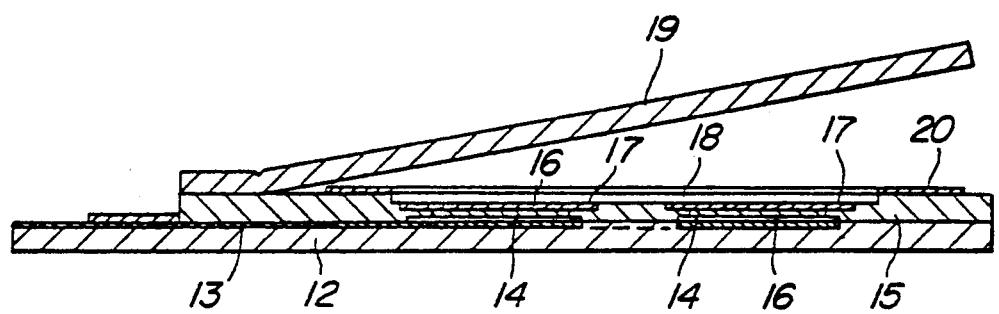
FIG. 4 is a sectional view of a second preferred embodiment of an electrode according to the present invention.

The preferred embodiments of the present invention will be initially described with reference to an embodiment having an internal solution for an electrode for measuring ion concentration.

Referring now to FIG. 3, which shows a compound electrode for use in the measurement of pH, reference numeral 1 designates a supporting cylinder or pipe formed of glass and the like, and reference numeral 2 designates an internal cylinder formed of glass and the like inserted into the supporting pipe 1. The inside cylinder 2 is provided with a responsive glass membrane 3 formed in an end portion thereof. Reference numeral 4 designates a silver wire inserted into the inside cylinder 2 and provided with an end portion thereof constructed as an internal electrode for use in the measurement. The wire 4 is coated at its end portion with silver chloride 5. Reference numeral 6 designates a gelatinized internal solution positioned in the inside cylinder 2 for coating the internal electrode 5 which is used in a measurement.

Reference numeral 7 designates another silver wire inserted into the supporting pipe 1 on the outside of the inside cylinder 2 and provided with an end portion, coated with silver chloride, and constructed as an internal electrode 8 for use as a reference electrode. Reference numeral 9 designates a gelatinized internal solution placed in the supporting pipe 1 so as to coat the end portion of the inside cylinder 2 and the internal electrode 8 used as a reference electrode and being partially exposed at an end of the supporting pipe 1 to construct a liquid junction surface 10.

The gelatinized internal solutions 6 and 9 are formed of a 3.3 M-aqueous solution of KCl (supersaturated by AgCl) and glycerine gelatinized with agar-agar. Gel-evaporation does not occur and the surface of the gelatinized internal solutions 6, 9 has been maintained under a wet condition even though they have been left unattended in air for a long time.

In the above described construction, the liquid junction 10 is formed as a part of the gelatinized internal solution 9 and its surface is maintained under a wet condition, so that the liquid junction 10 can be repeatedly used without cutting off a part thereof. In addition, even though air passes through the liquid junction 10 into the outside pipe 1 and the inside cylinder 2, the gelatinized internal solutions 6, 9 are not dried, so that measurement accuracy can be stabilized and it becomes unnecessary to further close up the closed portion of the outside pipe 1 and the inside cylinder 2 tight, whereby the manufacturing process can be simplified.

A 3.3 M-aqueous saturated solution of KCl (supersaturated by AgCl) with fine AgCl powders added and an aqueous solution of KCl having a concentration of 3.3M or less and other aqueous solutions, which can be used as an internal solution of an electrode for use in the measurement, can be used as the internal solution for the gelatinized internal solutions 6, 9.

Also ethylene glycol, diethylene glycol, triethylene glycol and derivatives thereof can be used as the gel-evaporation inhibitor in addition to the above described glycerine.

Also, other substances, for example gelatine, capable of gelatinizing internal solutions as well as the gel-evaporation inhibitor can be used as the gelatinizer and highly hygroscopic resins can be used together with the above described gelatinizers.

The quantities of the internal solution, the gel-evaporation inhibitor and the gelatinizer added are selected so that the internal solution and the gel-evaporation inhibitor can be gelatinized and the above described gel can be prevented from evaporating to maintain the surface of the gelatinized internal solutions 6, 9 under a wet condition in air.

The preferred embodiments of the above described quantities are as follows:

| | | |
|---|---|---|
| 1. Ethylene glycol 40 cc | Agar-agar 1 g | 3.3 M-aqueous solution of KCl 20 cc |
| 2. Diethylene glycol 25 cc | Agar-agar 1 g | 3.3 M-aqueous solution of KCl (supersaturated by AgCl) 5 cc |
| 3. Glycerine 40 cc | Agar-agar 1 g | 0.1 M-aqueous solution of KCl 20 cc |
| 4. Glycerine 35 cc | Agar-agar 1 g | 3.3 M-aqueous solution of KCl (supersaturated by AgCl) 25 cc |
| 5. Glycerine 40 cc | Gelatine 20 g | 3.3 M-aqueous solution of KCl (supersaturated by AgCl) 20 cc |

Each of the above described compositions was gelatinized to exhibit an appropriate hardness and maintained its surface under a wet condition after being left exposed in air. In order to prevent the surface of the gelatinized internal solutions 6, 9 from drying while they are left unattended at room temperature for a long time, a gel-evaporation inhibitor, such as glycerine, is preferably added to the internal solution, such as a 3.3 M-aqueous solution, at a ratio of 50% by volume or more.

Although in the above described preferred embodiment, a compound electrode for use in the measurement of pH was described, the present invention is applicable also to an ion electrode or reference electrode.

Figure 5:
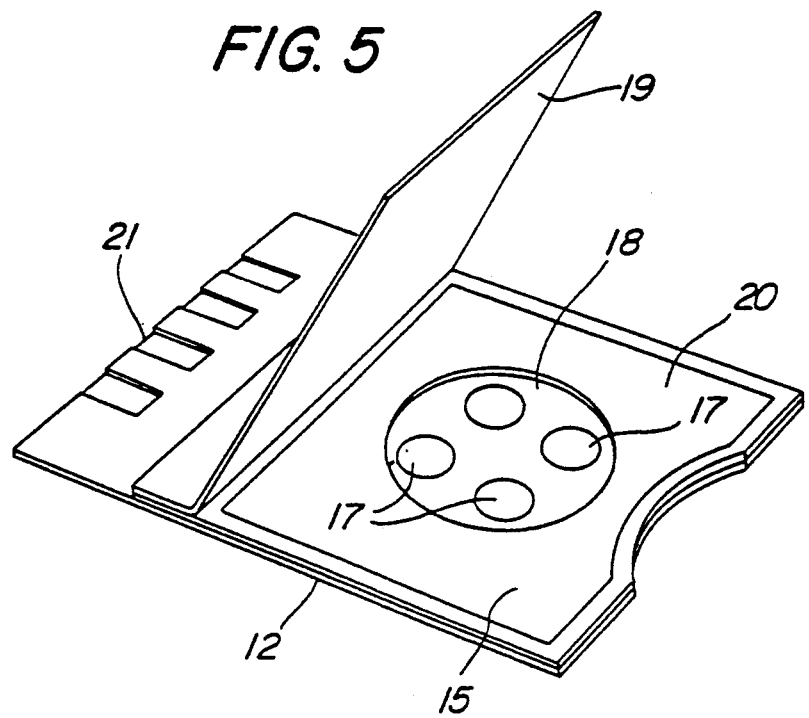
FIG. 5 is a perspective view of FIG. 4.

Another preferred embodiment of the present invention is described with reference to an electrode for use in the measurement of salts. Referring to FIGS. 4, 5, reference numeral 12 designates a planar substrate formed of vinyl chloride and the like, provided with a silver electrode 13 formed thereon by screen printing and internal electrodes 14 coated with silver chloride formed thereon at a plurality of places. Reference numeral 15 designates an upper supporting member made of vinyl chloride formed on the substrate 12 excepting the internal electrodes 14 formed by the screen printing and the like.

Reference numeral 16 designates a gelatinized internal solution, formed on top of each of the internal electrodes 14, which is the same as that in the above described preferred embodiment shown in FIG. 3. For example, the gelatinized internal solution 16 is heated to make a paste and then arranged on each internal electrode 14 by screen printing.

Reference numeral 17 designates a responsive membrane overlapped on each of the gelatinized internal solutions 16 and fixed with adhesives arranged on a circumference thereof while reference numeral 18 designates a measuring concave portion formed on a front surface side of the supporting member 15 of such a size that it can receive each responsive membrane 17 with a sample liquid being poured into the measuring concave portion 18. Reference numeral 19 designates a cover for the measuring concave portion 18 pivotally-mounted on the supporting member 15 at one end thereof and reference numeral 20 designates adhesives carried on a surface of the supporting member 15 to which the cover 19 is adhered so as to be able to seal up the measuring concave portion 18 tight. Reference numeral 21 designates a lead wire formed of the silver electrode 13 which can be attached as a male connector to suitable known circuits to process the measurement signals.

With this electrode for use in the measurement of salts, about one drop of the sample liquid is put in the measuring concave portion 18 and then spread out on each responsive membrane 17 by the cover 19. Subsequently, the cover 19 is fixed with the adhesives 20 to measure a salt-content of the sample liquid.

Since the surface of the gelatinized internal solution 16 is not dried in air before it is overlapped on the responsive membrane 17 in the manufacturing process, the electrode is easy to manufacture and a stabilized measurement can be attained.

According to the above preferred embodiments, an internal solution is gelatinized and a gel-evaporation inhibitor is added to the internal solution, so that a surface of the gelatinized internal solution is not dried out even after leaving the gelatinized internal solution unattended in air of a normal ambient temperature for a long time period to maintain a wet condition.

Accordingly, since a part of the above described gelatinized internal solution can be exposed during formation to form a liquid junction, it is unnecessary to renew the surface and its repeated use and preservation are easy. Also, in the case where the gelatinized internal solution is collectively housed in a cylinder, it is unnecessary to seal the cylinder and an electrode can be formed in the form of a thin film by screen printing and the like, so that an electrode for use in measurement can be small-sized and a stabilized measurement can be always attained.

Next, additional preferred embodiments of the present invention will be described below with reference to a sheet type compound electrode for use in the measurement of pH and the like.

Figure 6:
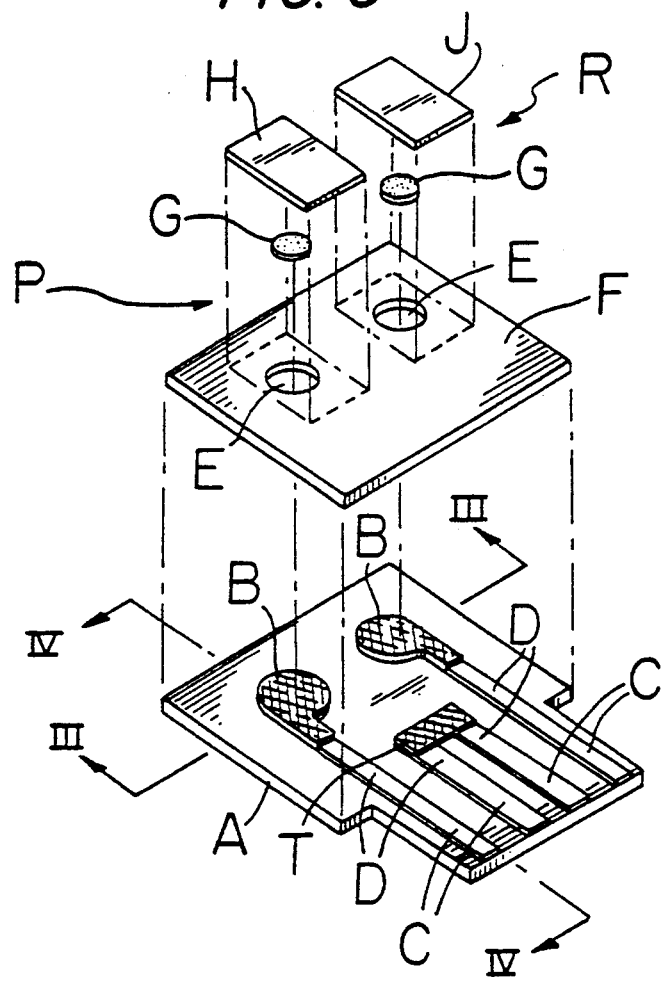
FIG. 6 is an exploded perspective view of a sheettype compound electrode according to the present invention.
Figure 7:
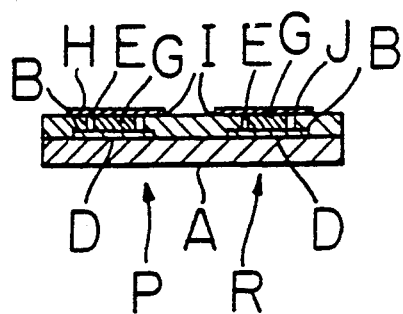
FIGS. 7 and 8 are sectional views of FIG. 6 taken along section lines III—III and IV—IV, respectively.
Figure 8:
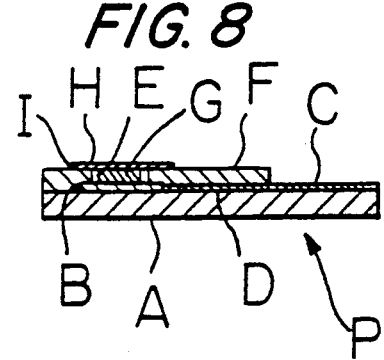

Referring to FIGS. 6 to 8, "A" designates a substrate formed of materials having a sufficiently high electrical insulating property, such as polyethylene terephthalate, even when impregnated in a solution containing electrolytes. The substrate A is provided with two pairs of electrodes "D", an inside pair of electrodes D and an outside pair of electrodes D, on an upper surface thereof. The electrodes can be formed by subjecting the upper surface of the substrate A to an anchoring or securing treatment by a silane-coupling agent and the like and graft processing and then adhering a paste containing electrically conductive substances, such as Ag, on the upper surface of the substrate A by a silk screen printing. In addition, base end portions positioned at one end edge portions of the substrates A of all electrodes D can be used as lead portions C as they are. The other nearly circular pointed end portions of the outside electrodes D are positioned at nearly central portions of the substrate A so as to form internal electrode portions B, B coated with an electrode material such as AgCl while a temperature-compensating electrode portion T, such as a thermistor, is formed over the space between the other pointed end portions positioned at a nearly central portion of the substrate A of the inside pair of electrodes D, D.

A support layer F (in this example a polyethylene terephthalate layer) formed of materials having a sufficiently high electrical insulating property, similarly to the substrate A, and provided with holes E, E at places corresponding to said internal electrode portions B, B is formed on the upper surface of the substrate A by a screen printing method of a thermal fusion method of using adhesives (for example, polyolefine series adhesives, silicon resin series adhesives and the like) capable of securing a sufficiently high electrical insulating property (for example 10 MΩ or more) while exposing all of the lead portions C and their circumference. In addition, also the upper surface of this support layer F is subjected to a graft processing and anchor treatment by silane coupling agents and the like.

Furthermore, gelatinized members G, G formed in a predetermined or appointed shape (in this example, a disc having a diameter of 5 mm and a thickness of about 0.2 mm) from a uniform mixture comprising a basic internal solution (for example a 3.3 M-aqueous solution of KCl supersaturated by AgCl with a phosphoric acid-buffer solution added), a gelatinizer, such as agar-agar and gelatine, and a moisture-evaporation inhibitor, such as glycerin and propylene glycol, is put in both holes E, E of the support layer F. The gelatinized member can be heated to form a paste and then using a screen printing method so that their upper surface may be slightly projected over the upper surface of the support layer F and they may be overlapped on the internal electrode portions B, B.

In addition, a flat plate-like pH-responsive glass membrane H is produced by subjecting a flat plate-like super-thin glass, previously molded so as to have an appointed size, e.g. 10 mm long, 8 mm wide and 0.1 mm thick, to a high-speed surface heating treatment with preheating, and is adhered to the upper surface of the support layer F along the circumference thereof over the gelatinized member G. An internal solution is put into one of the holes E, E. The glass member H is fastened by the use of adhesives I having a sufficiently high electrical insulating property (for example, a silicon series, epoxy series and urethane series of organic high molecular adhesives containing silane coupling agents and the like) so that a lower surface of the flat plate-like pH-response glass membrane H may be contacted to an upper surface of the gelatinized member G used as the internal solution and the gelatinized member G for use in the internal solution is sealed hermetically in the hole E, thereby forming a glass electrode portion P for use in the measurement of pH.

A liquid junction membrane J, formed of inorganic sintered porous substances, organic high molecular porous substances and the like is impregnated with KCl and is adhered to the upper surface of the support layer F along the circumference thereof over the gelatinized member G which is used as the internal solution in the other hole E. A lower surface of the membrane J may be contacted to the upper surface of the gelatinized member G of the internal solution, thereby forming a reference electrode portion R. However, since the gelatinized member G is used for the internal solution in the above described manner, this liquid junction membrane J may be omitted.

Figure 9:
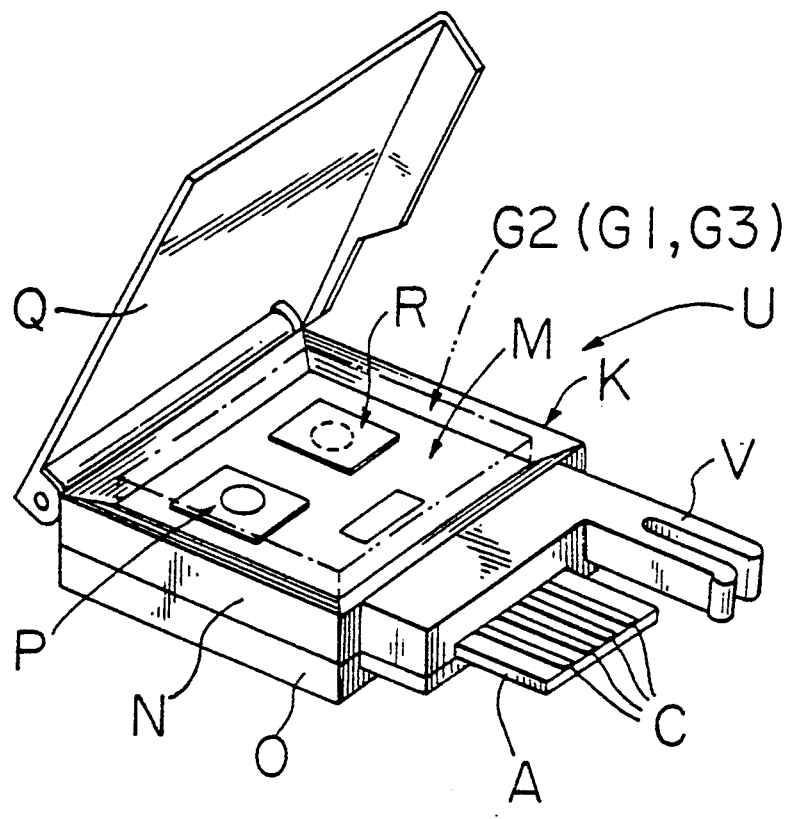
FIG. 9 shows the electrode of FIG. 6 mounted in a housing K to form a measuring unit U.

The electrode, for use in the measurement of ions constructed in the above described manner, has a total thickness of about 0.5 mm and is housed in a casing K formed of synthetic resins (having a depth of 23 mm, a width of 23 mm and a height of 7 mm in The glass electrode portion P and reference electrode portion R is positioned on the upper surface side. On one projecting end edge portion of the substrate A, lead portions C are formed to create a male connector for the removable measuring electrode module unit U as shown in FIG. 9. The exterior casing K, composing the module measuring electrode unit U comprises an upper frame member N forming a depressed planar portion M for pouring a sample liquid thereinto, a bottom cover O for the upper frame member N and an upper cover Q for the depressed portion M for pouring a sample liquid mounted on the upper frame member N at one end edge portion thereof so as to be freely swung to open and close. In addition, an engaging projection member V for providing a fastening contact with an aperture in the main body Z of the measuring apparatus, which will be mentioned later, extends from an end edge of the upper frame member N of the casing K on the same side from which the lead portions C are projected.

Figure 10:
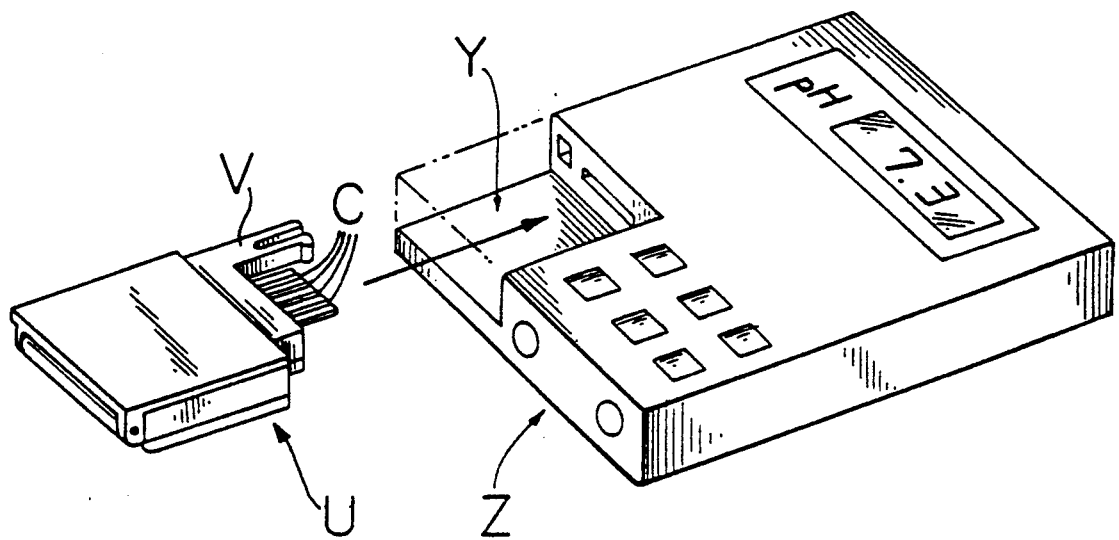
FIG. 10 depicts the use of measuring unit U of FIG. 9 relative to the main body Z of a measuring apparatus.

In operation of the measuring unit U, including the electrode for use in the measurement of ions, the upper cover Q is opened and one drop or several drops of the sample liquid are poured into the depressed or concaved portion M to contact the glass electrode P and the reference electrode R positioned in the planar bottom portion of the concaved portion and then the upper cover Q is closed. Subsequently, the measuring electrode unit U is inserted into a fitting portion Y of the body Z of the measuring apparatus, constructed to have a liquid crystal display through the lead portions and the engaging projection member V, as shown in FIG. 10, to measure a pH of the sample liquid.

The preservation of the electrode for use in the measurement of ions in the measuring electrode unit U while it is not being used as well as the calibration of pH of the glass electrode portion P, before and after the measurement can be carried out by the following novel means.

Figure 11A:
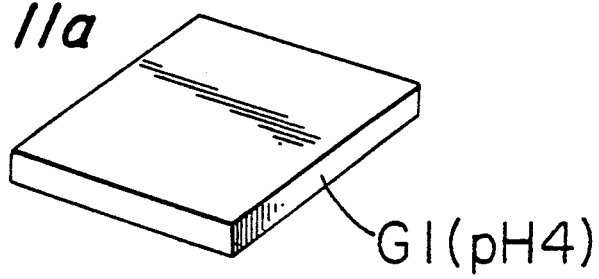
FIGS. 11A-C depict gelatinized members of a predetermined shape for removable insertion into a concave portion M of the casing K shown in FIG. 9 for the purpose of preserving or calibrating electrodes located at the bottom of the concave portion M (as suggested by the dashed lines of FIG. 9)
Figure 11B:
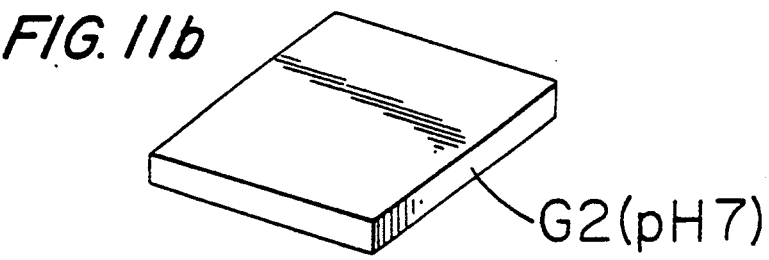
Figure 11C:
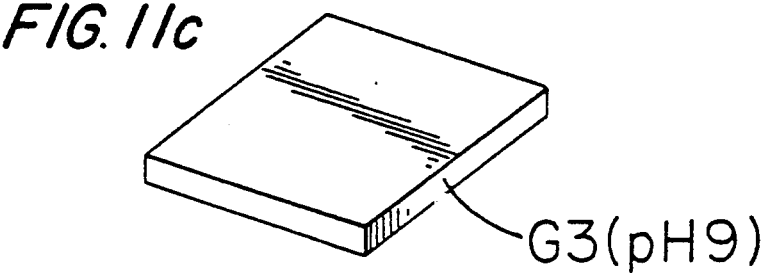

Plural kinds of gelatinized members (for example, G1 having a pH of 4, G2 having a pH of 7 and G3 having a pH of 9) are prepared by mixedly adding a gelatinizer, such as agar-agar and gelatine, and a moisture-evaporation inhibitor, such as glycerine and ethylene glycol, to an aqueous solution comprising an internal solution or a buffer solution or a pH-adjusting solution or the like or the combinations thereof to gelatinize. The pH of the resulting gelatinized solution is set and the gelatinized solution is molded in a predetermined shape, as shown in for example, FIG. 11 (in this example, a rectangular shape having a depth of about 15 mm, a width of about 15 mm and a height of about 2 mm). The predetermined shape is capable of being inserted into the concaved portion M which receives the sample liquid of the casing K.

For the preservation of the electrode, while it is not being used, the gelatinized member G2 (having a pH of 7) is inserted into the concaved portion M for pouring the sample solution of the casing K (that is, placed on the glass electrode portion P and the reference electrode portion Q) and then the upper cover Q is closed, as shown by an imaginary line in FIG. 9. In addition, in the pH-calibration of the glass electrode portion P, the gelatinized members G1, G2, G3 are inserted into the concaved portion M (that is, placed on the glass electrode portion P and the reference electrode portion R) also as shown by an imaginary line in the FIG. 9 to carry out the measurement in the same procedure as in the measurement of the sample solution. In addition, in this case, it goes without saying that the gelatinized members G1, G2, G3 have a function as a pH-calibrating gelatinized member, respectively. The gelatinized member G2 (having a pH of 7) has also a function as a preserving gelatinized member common to the glass electrode portion P and the reference electrode portion R.

Next, a preferred embodiment of a calibrating standard sample according to the present invention is described with reference to FIG. 12.

Referring now to FIG. 12, reference numeral 101 designates a rod-like gelatinized standard solution obtained by adding glycerine as a gel-evaporation inhibitor to a calibrating standard solution such as KCl and gelatinizing the mixture with agar-agar. Reference numeral 102 designates a traveling vessel into which one end of the gelatinized standard solution is fixedly inserted. Reference numeral 103 designates an engaging projection projecting from an outside surface of a circumferential wall of the traveling vessel 102.

Reference numeral 104 designates an inside cylinder, into which both the traveling vessel 102 and the gelatinized standard solution 101 are slidably inserted, the inside cylinder 104 being provided with a slit 105 in a direction of axis shaft line thereof, and said engaging projection 103 being slidably inserted into the slit 105. Reference numeral 106 designates a cylindrical pickup member fixedly mounted on a side end portion of a bottom of the inside cylinder 104. Reference numeral 107 designates an outside cylinder, into which an engaging pipe 108 is fixedly inserted, and the engaging pipe 108 is provided with a spiral groove 109 formed on an inside circumferential surface thereof.

The inside cylinder 104 is rotatably inserted into the engaging pipe 108 and a pointed end of the engaging projection 103 is inserted into the spiral groove 109. The outside cylinder 107 is supported by the pickup member 106 together with the engaging pipe 108 at one end thereof and an engaging projection 110 formed on a periphery of a pointed end portion of its inside cylinder 104 is engaged with the other end of the engaging pipe 108, whereby the outside cylinder 107 is mounted on the inside cylinder 104. Reference numeral 111 designates a closure cap.

When the gelatinized standard solution 101 is used, the cap 111 is removed and then the outside cylinder 107 is rotated while fixing the pickup member 106. Thereupon, the engaging projection 103 is moved along the slit 105 by rotating the spiral groove 109, whereby the gelatinized standard solution 101 is projected out of the outside cylinder 107, as shown by a chain line, so that the responsive portion of the ion-measuring electrode to be calibrated is brought into contact with the surface of the gelatinized standard solution.

When the gelatinized standard solution is preserved or carried about, it is housed in the inside cylinder 104 collectively, as shown by a full line on FIG. 12. Accordingly, the gelatinized standard solution 101 is protected by the cap 111, the inside cylinder 104 and the like, so that it can be easily preserved and carried about.

Also ethylene glycol, diethylene glycol, triethylene glycol, derivatives thereof and the like can be used as the gel-evaporation inhibitor in addition to the above described glycerin. Every gelatinizer, for example gelatine, capable of gelatinizing standard solutions and gel-evaporation inhibitors can be used. Also the use of highly hygroscopic resins together with the gelatinizer is possible.

The standard solution, the gel-evaporation inhibitor and the gelatinizer are used in such a quantity that the standard solution and the gel-evaporation inhibitor can be gelatinized, the gel can be prevented from evaporating, and the surface of the gelatinized standard solution can be maintained under a wet condition in air of ordinal temperature.

In the event that an aqueous solution of KCl is used as the standard solution, specific examples of the above described composition are as follows:

| 1. Ethylene glycol 40 cc | Agar-agar 1 g | 3.3 M-aqueous solution of KCl 20 cc |
|---|---|---|
| 2. Diethylene glycol 25 cc | Agar-agar 1 g | 3.3 M-aqueous solution of KCl (AgCl-supersaturated) 5 cc |
| 3. Glycerine 40 cc | Agar-agar 1 g | 0.1 M-aqueous solution of KCl 20 cc |
| 4. Glycerine 35 cc | Agar-agar 1 g | 3.3 M-aqueous solution of KCl (AgCl-supersaturated) 25 cc |
| 5. Glycerine 40 cc | Gelatine 20 g | 3.3 M-aqueous solution of KCl (AgCl-supersaturated) 20 cc |

The above described compositions were all gelatinized with a hardness suitable to handle and their surface was maintained under a wet condition for a long time in air of normal temperature.

The gel-evaporation inhibitor, such as glycerine, is preferably added to the standard solution, such as a 3.3 M-aqueous solution of KCl, at a ratio of 50% or more by volume in order to prevent the surface of the gelatinized standard solution 101 from being dried also in the event that the gelatinized standard solution 101 is left unattended for a long time in air of normal temperature. Although an aqueous solution of KCl was used as the standard solution in the above described compositions, other standard solutions may be used.

FIGS. 13, 14 show a second preferred embodiment of a calibrating standard sample according to the present invention.

Referring to FIGS. 13, 14, reference numeral 121 designates a rod-like gelatinized standard solution which is the same as in the above described first preferred embodiment. Reference numeral 122 designates a traveling member on which an end portion of the gelatinized standard solution 121 is fixedly mounted. Reference numeral 123 designates a cylindrical member, the gelatinized standard solution 121 and the traveling member 122 being slidably inserted into the cylindrical member 123, and a projection 124, which is formed on an inside surface of the cylindrical member 123 in the direction of an axis shaft line thereof, being engaged with a concaved groove 125 formed in the traveling member 122.

Reference numeral 126 designates a pickup member, a screw shaft 127 fixedly projecting from the pickup member 126 being passed through a bottom wall of the cylindrical member 123, the screw shaft 127 being rotatably and detachably mounted on the cylindrical member 123 by means of an engaging projection 128 provided on the screw shaft 127, the screw shaft 127 being screwed in a threaded hole 129 of the traveling member 122, and the screw shaft 127 being inserted into the gelatinized standard solution 121. Reference numeral 130 designates a cap.

In this preferred embodiment, upon fixing the cylindrical member 123 and rotating the pickup member 126, the gelatinized standard solution 121 is projected out of the cylindrical member 123 and enters the cylindrical member 123, again together with the traveling member 122, by the rotation of the screw shaft 127.

A calibrating standard sample according to the present embodiment is obtained by gelatinizing a calibrating standard solution with a gelatinizer and housed in a cylindrical vessel so as to be taken in and out, so that it can be reduced in volume, whereby its preservation and carrying can be simplified. It is only necessary for the calibration of an ion-measuring electrode to bring a responsive portion of the ion-measuring electrode into contact with a surface of the gelatinized standard solution. Accordingly, the calibrating standard sample according to the present invention is simple in use.

In addition, a gel-evaporation inhibitor is added to the gelatinized standard solution to prevent it from being dried so that its surface may be always maintained under a wet condition, so that a highly accurate calibration can be attained. Besides, since it is unnecessary to close up a vessel air tight, a cylindrical vessel having an optional construction can be used, that is to say the vessel can be simplified in construction. Furthermore, since the gelatinized standard solution is housed in the cylindrical vessel in the form of a rod so as to be taken in and out, it is easy to repeatedly use it.

A gelatinized member for an electrode for use in the measurement of ions according to the present invention is below described with reference to another preferred embodiment. FIG. 15 shows a gelatinized member 201 for use in an internal solution.

A high humidity-holding water-contained jelly, such as U-jelly (a trademark of a commodity developed recently by Showa Denko Co., Ltd. of Japan), mainly comprises an acrylic polymer dissolved in an internal solution comprising, for example, a 3.3 M-aqueous solution of KCl supersaturated by AgCl with a phosphoric acid-buffer solution added and then the resulting solution is gelatinized by adding a gelatinizer selected from a group consisting of agar-agar, gelatine, glue, alginic acid and the like. Subsequently, the gelatinized product is molded in a predetermined shape (in this example, in a disc-like shape for a sheet type electrode for use in the measurement of ions, as shown in the above described FIGS. 6 to 8, having a diameter of about 5 mm and a thickness of about 0.1 to 0.2 mm) by cutting, molding and the like.

Figure 16:
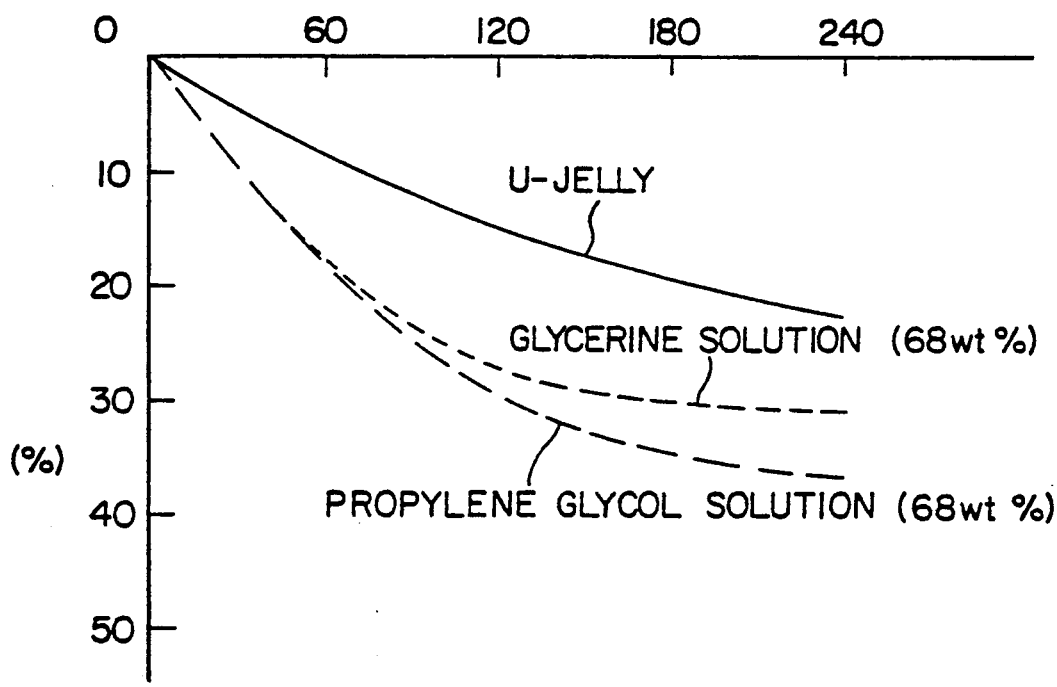
FIG. 16 shows a graph which depicts the superior weight-reduction characteristics of U-jelly relative to glycerine and propylene glycol.

The U-jelly, as a high humidity-holding water-contained jelly, was originally developed by Showa Denko Co., Ltd. as a base agent for a cosmetic cream. It is a transparent water-contained jelly mainly comprising sodium salt with an acrylic polymer having a remarkably high compatibility with other aqueous solutions and remarkably superior to conventional moisture-evaporation inhibitors, such as glycerin and propylene glycol, in moisture-holding function and vapor pressure equilibrium-holding function due to the formation of clusrate by hydrogen bond between polymeric molecules, as obvious from one characteristic example shown in FIG. 16 wherein axis of the ordinate indicates a weight-reduction rate while the axis of the abscissa indicates time in minutes. Accordingly, this jelly can maintain a sufficient lubricity for a long time without drying out even though it is exposed to air for a long time and absorption of water in air and dewing are hardly produced and as a result, it has a characteristic that its surface can be always maintained under a moderate wet condition.

Figure 17:
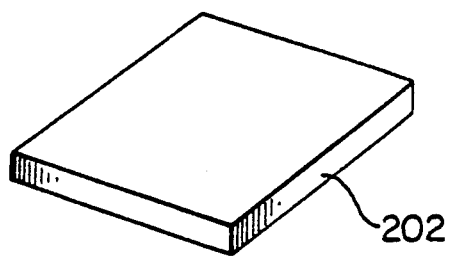
FIG. 17 shows a gelatinized member having a predetermined shape for use in the calibration or storage of an electrode.

FIG. 17 shows a gelatinized member 202 for use in the calibration of pH of an electrode according to another preferred embodiment (however, if a pH is selected at about 7, it can be used also as a gelatinized member for use in the preservation of an electrode). High humidity-holding water-contained jelly (U-jelly) mainly comprising an acrylic polymer likewise in the above described preferred embodiment is dissolved in a predetermined aqueous solution comprising a buffer-solution selected from a group consisting of phosphoric acid, hydrochloric acid, acetic acid, potassium hydrogen phthalate, potassium bihydrogen citrate and the like and a pH-adjusting solution selected from a group consisting of aqueous solutions of potassium chloride (KCl), sodium hydroxide, sodium tetraborate, sodium acetate, sodium carbonate and the like at a suitable ratio and then, the resulting solution is gelatinized by adding a gelatinizer selected from a group consisting of agar-agar, gelatine, glue, alginic acid and the like. Subsequently, the gelatinized product is molded so as to have an appointed pH (for example pH of 4, pH of 7 and pH of 9) and an appointed shape (in this example, rectangular shape having a depth of about 15 mm, a width of about 15 mm and a height of about 22 mm capable of inserting into a concaved portion M for pouring the sample liquid of the casing K constructing the measuring electrode unit U as shown in the above described FIG. 9).

Each of the gelatinized members 202, of which pH was set at these appointed pH values (4, 7, 9), is satisfactorily used in the preservation of the electrode for use in the measurement of ions in the measuring electrode unit U while it is not being used and the pH-calibration of the glass electrode portion of the electrode for use in the measurement of ions in the same manner as in the gelatinized members G1, G2, G3 described already.

In addition, although it is desired that the gelatinized member having a pH of 7 is used as the gelatinized member 202 for use in the preservation of the electrode common to the glass electrode and reference electrode, it is not always necessary that the gelatinized member 202 has a pH of 7 strictly. Besides, there is not any harm if the pH-value is not exactly 7.

Nextly, the results of the investigation of the change of pH-value with a lapse of time for several kinds of gelatinized member 202 for use in the pH-calibration as described.

Samples, such as :
1. a mixture comprising U-jelly (pH of 7.4) of 34 g, a 0.25 M-phosphoric acid-buffer solution (pH of 6.92) of 6 g containing a 3.3. M-aqueous solution of KCl and agar-agar of 0.5 g,
2. a mixture comprising U-jelly (pH of 7.4) of 28 g, a 0.25 M-phosphoric acid-buffer solution (pH of 7.13) of 12 g containing a 3.3 M-aqueous solution of KCl and agar-agar of 0.5 g,
3. a mixture comprising U-jelly (pH of 7.4) of 20 g, a 0.25 M-phosphoric acid-buffer solution (pH of 7.13) of 20 g containing a 3.3 M-aqueous solution of KCl and agar-agar of 0.5 g, were heated at about 100° C. to dissolve the agar-agar and then to spread the mixtures over a flat plate having a size of about 30 cm×30 cm. Subsequently, a spacer of about 2 mm was placed on the flat plate and a glass plate was placed on the spacer to cool and gelatinize. Then, the gelatinized product was cut into predetermined shapes (such as a rectangular shape having a depth of about 15 mm, a width of about 15 mm and a height of about 2 mm) and tested on pH immediately after the preparation of the gelatinized member and after a lapse of an appointed period.

As a result, it was found, as shown in the following table, that an initial pH is very stably maintained and hardly changed over a long period of time.

SAMPLE TABLE
Measured pH-Value

| Sample | Immediately After Preparation | After 8 Days | After One Month |
|--------|-------------------------------|--------------|-----------------|
| 1 | 6.76 | — | 6.77 |
| 2 | 7.03 | 6.98 | — |
| 3 | 6.95 | 6.96 | — |

Figure 18:
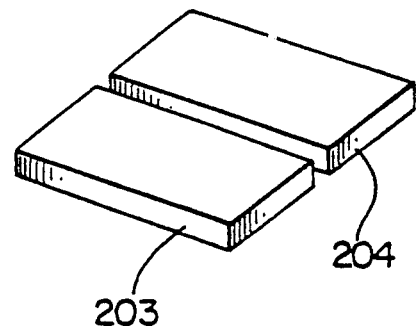
FIG. 18 shows a pair of gelatinized members having a predetermined shape, one member for use in the preservation of a glass electrode and one member for use in the preservation of a reference electrode.

In addition, although in the above described preferred embodiment the gelatinized member 202 having a pH adjusted at 7 and molded in a rectangular shape having a size of about 15 mm deep, about 15 mm wide and about 2 mm high (so as to be inserted into the concaved portion M for receiving the sample liquid as shown in the above described FIG. 9) was used as the gelatinized member for use in the preservation of electrode common to the glass electrode and the reference electrode, it may be constructed with the gelatinized member 203 for use in the preservation of a glass electrode and a gelatinized member 204 for use in the preservation of a reference electrode divided, as shown in FIG. 18. In this case, the gelatinized member 203 for use in the preservation of a glass electrode is adjusted in pH at 7 and the gelatinized member 204 for use in the preservation of a reference electrode comprises the same composition as the gelatinized member 201 for use in the internal solution in the above described preferred embodiment. The gelatinized members 203, 204 can be molded to a size nearly half that of the gelatinized member 202 (that is to say, in a rectangular shape having a depth of about 15 mm, a width of about 7 mm and a height of about 2 mm), respectively.

Besides, the surface of all the gelatinized members 201, 202, 203, and 204 for use in the measurement of ions according to the above described preferred embodiments can be always maintained under a moderate wet condition (not excessively soft and sticky, but moist and firm) for a long time on account of the superior vapor-pressure equilibrium condition holding function of U-jelly added to the gelatinized members. However, for example in order to increase contact to the electrode surface, a small amount of a hygroscopic substance (such as glycerin) may be added to finely adjust the wet condition of the surface if necessary.

As obvious from the detailed description, in a gelatinized member for an electrode for use in the measurements of ions according to the preferred embodiments, a high humidity-holding water-contained jelly mainly comprising an acrylic polymer is more superior to glycerine or propylene glycol in a moisture-holding function and vapor-pressure equilibrium state holding function is used as a moisture-evaporation inhibitor to be added to the gelatinized member. Its surface can be always maintained under a moderate wet condition, whereby the desired functions can be stably exhibited for a long time without producing any deterioration such as a change in concentration (change in pH). Accordingly, superior effects are exhibited in that a gelatinized member according to the present invention can be very satisfactorily used as a member for use in an internal solution of a glass electrode and a reference electrode for the glass electrode, a member for use in the preservation of an electrode and a member for use in the pH-calibration particularly in the case where a sheet type electrode for use in the measurement of ions is constructed.

While the above embodiment has been disclosed as the best mode presently contemplated by the inventors, it should be realized that this example should not be interpreted as limiting because artisans skilled in this ion-concentration instrumentation field, once given the present teaching, can vary from the specific embodiments.

What is claimed is:

1. A removable sample testing member for use with a compact ion-concentration measuring apparatus which provides an indication of an ion-concentration of a sample, comprising:
   a nonconductive nonapertured planar substrate having an outer edge and an upper surface;
   first and second lead portions carried by the upper surface of said substrate from the outer edge of said substrate to first and second internal positions, respectively;
   first and second internal electrode portions formed at the first and second internal positions of said first and second lead portions, respectively;
   a nonconductive support layer having a lower surface and an upper surface, the lower surface of said support layer adhered to the upper surface of said substrate and thereby sandwiching said first and second lead portions between said substrate and said support layer, said support layer having an exterior edge which terminates before the outer edge of said substrate to expose a part of said substrate and a part of the lead portions of said first and second lead portions for physical and electrical connection to the ion-concentration measuring apparatus;
   first and second holes provided in said support layer spatially corresponding to said first and second internal electrode portions whereby said internal electrode portions are respectively accessible through said holes;
   a glass electrode portion comprised of a first gelatinized member located in said first hole and contacting said first internal electrode portion, the gelatinized member being of a thickness to project an upper surface thereof slightly above the upper surface of said support layer, and a PH-responsive glass membrane overlaying said first hole, said PH-responsive glass membrane contacting the upper surface of said first gelatinized member and hermetically sealing said first gelatinized member in said first hole; and
   a reference electrode portion comprised of a second gelatinized member located in said second hole and contacting said second internal electrode portion.

2. The removable sample testing member of claim 1 wherein the gelatinized members are formed with an acrylic polymer with sodium.

3. The removable sample testing member of claim 1 wherein said gelatinized members have a thickness of less than 1 mm.

4. The removable sample testing member of claim 1 wherein said first and second lead portions are respectively comprised of an electrically conductive substance silkscreened onto the upper surface of said substrate.

5. The removable sample testing member of claim 1 wherein said first and second gelatinized members are respectively comprised of an internal solution silkscreened into said first and second holes.

6. The removable sample testing member of claim 1 wherein said second gelatinized member is of a thickness to project an upper surface thereof slightly above the upper surface of said support layer, and further comprising:
a liquid junction membrane overlaying the second hole and contacting the upper surface of said second gelatinized member.

7. The removable sample testing member of claim 1 further comprising:
third and fourth lead portions located on the upper surface of said substrate from the outer edge of said substrate to third and fourth internal positions, respectively; and
a temperature-compensating electrode portion formed across the third and fourth internal positions of said third and fourth lead portions.

8. The removable sample testing member of claim 7 wherein said third and fourth lead portion are comprised of an electrically conductive substance silkscreened onto the upper surface of said substrate.

* * * * *